(12) United States Patent
Borland et al.

(10) Patent No.: US 11,581,160 B2
(45) Date of Patent: Feb. 14, 2023

(54) METHODS AND SYSTEMS FOR X-RAY TUBE WITH TEXTURING

(71) Applicant: GE Precision Healthcare LLC, Milwaukee, WI (US)

(72) Inventors: Andrew Jay Borland, Whitefish Bay, WI (US); Andrew Marconnet, Mukwonago, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 374 days.

(21) Appl. No.: 16/800,432

(22) Filed: Feb. 25, 2020

(65) Prior Publication Data

US 2021/0265127 A1  Aug. 26, 2021

(51) Int. Cl.
*H01J 35/06* (2006.01)
*A61B 6/03* (2006.01)
(Continued)

(52) U.S. Cl.
CPC ............ *H01J 35/066* (2019.05); *A61B 6/032* (2013.01); *B23P 9/04* (2013.01); *C23F 1/02* (2013.01); *H01J 9/02* (2013.01); *H01J 35/064* (2019.05)

(58) Field of Classification Search
CPC . A61B 6/10; A61B 6/107; A61B 6/032; H01J 1/02; H01J 1/04; H01J 1/06; H01J 1/066; H01J 5/02; H01J 5/04; H01J 5/08; H01J 5/10; H01J 9/04; H01J 9/24; H01J 9/30; H01J 19/02; H01J 19/04; H01J 19/06; H01J 19/066; H01J 19/10; H01J 19/12; H01J 19/14; H01J 19/20; H01J 19/48; H01J 19/54; H01J 19/56; H01J 19/57; H01J 29/06; H01J 29/48; H01J 29/484; H01J 29/485; H01J 29/84; H01J 29/86; H01J 29/861; H01J 29/88; H01J 35/02; H01J 35/04; H01J 35/06; H01J 35/066; H01J 37/04; H01J 37/06; H01J 37/065; H01J 37/07; H01J 37/09; H01J 2201/02; H01J 2201/19; H01J 2201/342; H01J 2201/3421; H01J 2201/3425; H01J 2203/02; H01J 2209/02; H01J 2223/02; H01J 2223/04; H01J 2223/12; H01J 2229/0007;
(Continued)

(56) References Cited

U.S. PATENT DOCUMENTS 5,629,970 A  5/1997  Woodruff et al.
6,263,045 B1  7/2001  Lipkin et al.
(Continued)

FOREIGN PATENT DOCUMENTS

CN   111883407 A * 11/2020 ................ H01J 1/88

OTHER PUBLICATIONS

EP application 21158474.3 filed Feb. 22, 2021—Extended Search Report dated Jul. 21, 2021; 9 pages.

*Primary Examiner* — Kiho Kim
(74) *Attorney, Agent, or Firm* — McCoy Russell LLP

(57) ABSTRACT

Various methods and systems are provided for a cathode cup having a surface texturing to aid in adherence of emitter deposited films. In one embodiment, a method may include chemically and/or mechanically texturing a surface of a cathode cup to form a plurality of features with a higher than threshold depth of each feature, the surface of the cathode cup facing an emitter coupled to the cathode cup.

18 Claims, 10 Drawing Sheets

(51) Int. Cl.
*C23F 1/02* (2006.01)
*H01J 9/02* (2006.01)
*B23P 9/04* (2006.01)

(58) Field of Classification Search
CPC .......... H01J 2229/0092; H01J 2229/48; H01J 2229/4803; H01J 2229/4806; H01J 2229/4824; H01J 2229/4831; H01J 2229/4844; H01J 2229/58; H01J 2229/583; H01J 2229/86; H01J 2229/863; H01J 2229/8632; H01J 2229/8633; H01J 2229/8636; H01J 2229/8637; H01J 2229/88; H01J 2229/8924; H01J 2235/06; H01J 2235/165; H01J 2235/166; H01J 2235/167; H01J 2235/168; H01J 2237/02; H01J 2237/0203; H01J 2237/0206; H01J 2237/0213; H01J 2237/022; H01J 2237/026; H01J 2237/028; H01J 2237/03; H01J 2237/032; H01J 2237/31; H01J 2237/3114; H01J 2237/3151; H01J 2237/316; H01J 2237/31732; H01J 2237/31735; H01J 2237/3174; H01J 2893/0001; H01J 2893/0002; H01J 2893/0005; H01J 2893/0006; H01J 2893/0012; H01J 2893/0019; H01J 2893/0022; H01J 2893/0023; H01J 2893/005; H01J 2893/0074; H01J 2893/0077; H01J 2893/0084; H01J 9/02; H01J 35/064; H01J 9/042; H01J 2201/34; B23P 9/04; C22F 1/10; C23C 22/27; C23F 1/02; C23F 4/04
See application file for complete search history.

(56) References Cited

U.S. PATENT DOCUMENTS 8,548,124 B2    10/2013    Hauttmann et al.
2007/0269015 A1  11/2007    Raber et al.

* cited by examiner

METHODS AND SYSTEMS FOR X-RAY TUBE WITH TEXTURING

FIELD

Embodiments of the subject matter disclosed herein relate to methods and systems for x-ray systems and, more particularly, to a cathode cup having a surface finish or texturing to aid in adherence of emitter deposited films.

BACKGROUND

Noninvasive imaging modalities may transmit energy in the form of radiation into an imaging subject. Based on the transmitted energy, images may be subsequently generated indicative of the structural or functional information internal to the imaging subject. Electron sources are employed in x-ray systems, such as computed tomography (CT) and cardiovascular (CV) systems. Electron sources usually comprise of thermionic emitters which emit electrons upon reaching a certain temperature. The filaments forming these thermionic emitters may be made of metal with a high melting point, like tungsten, lanthanum, or their alloys.

The radiation source such as an x-ray source typically comprises an x-ray tube including a cathode assembly having an emitter fixed in a cup oriented to face an anode, or target, which is typically a metal or composite structure electrically connected to a high-voltage electrical circuit. The space between the cathode and anode is evacuated. The cathode cup is designed to produce a tailored electric potential distribution in the vacuum such that all electron trajectories are redirected from their initial divergent motion toward a focal spot on the anode surface. Upon energization of the electrical circuit, which produces a potential difference of, for example, 60 kV to 140 kV, electrons are directed from the cathode to the anode. The electrons strike the anode (target) and produce high-frequency electromagnetic waves, such as x-rays, and residual thermal energy. The residual energy is absorbed by the components within x-ray tube as heat.

During operation of the x-ray system, certain portion of the x-ray tube such as the emitter material may be exposed to high temperatures. Such elevated temperatures may cause material from the emitter to sublimate. A reliable process is employed to contain the sublimated material.

BRIEF DESCRIPTION

In one embodiment, a method comprises: chemically and/or mechanically texturing a surface of a cathode cup to form a plurality of features with a higher than threshold depth of each feature and greater than a threshold distance between two adjacent features, the surface of the cathode cup facing an emitter coupled to the cathode cup.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 3:
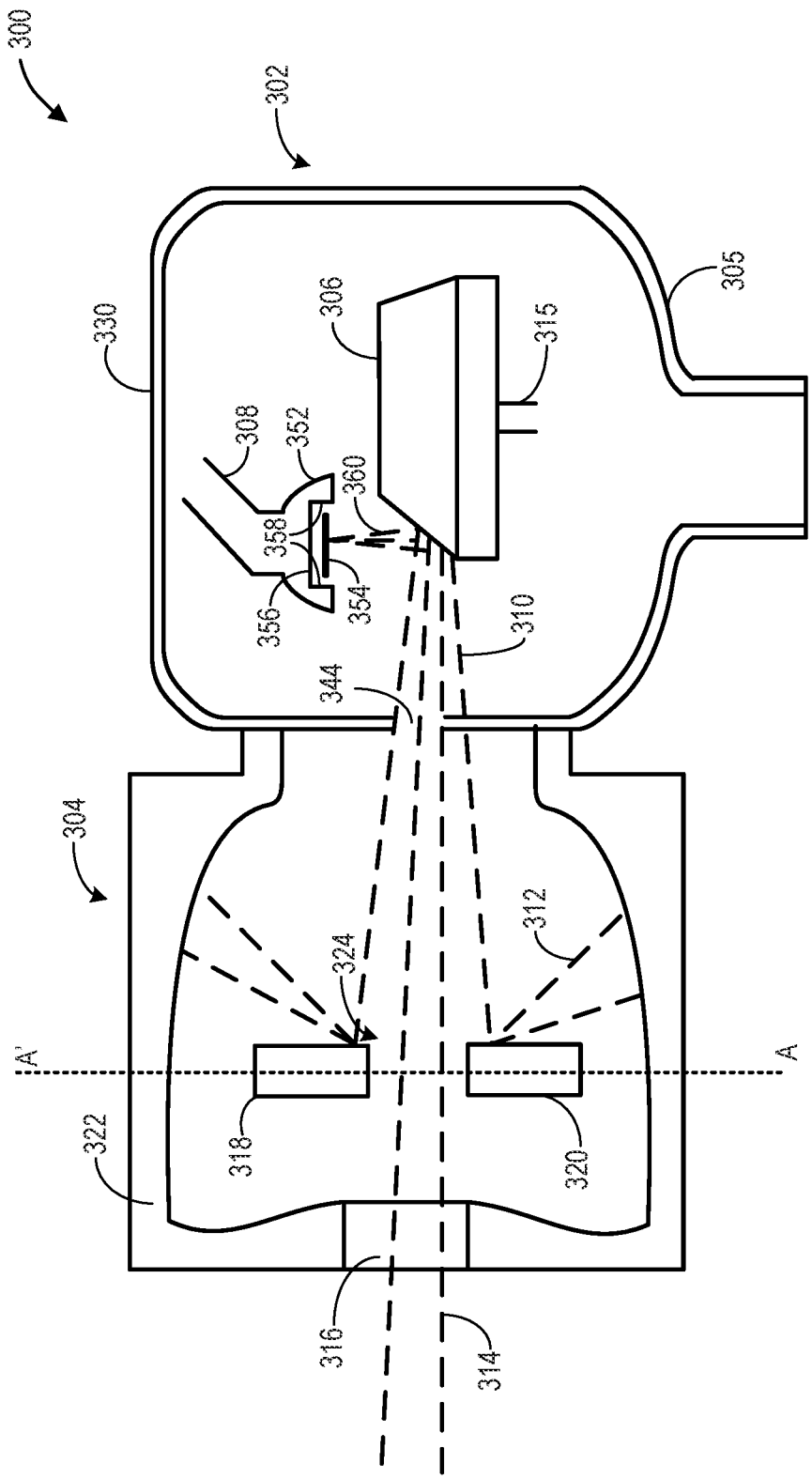
FIG. 3 shows a schematic diagram of a radiation source used in the imaging system.
Figure 5:
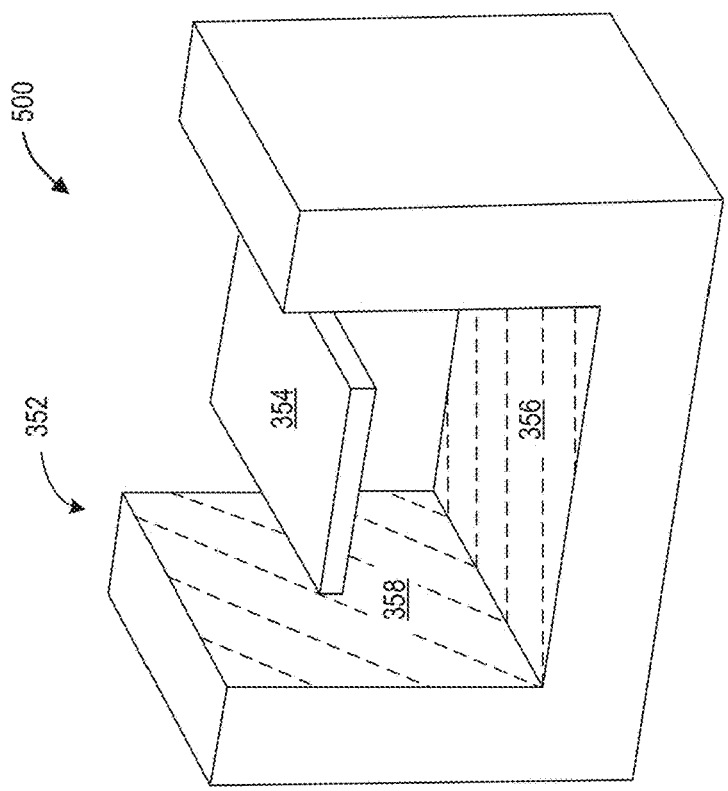
FIG. 5 shows an isometric view of a texture on a cathode cup according to the present disclosure.
Figure 4:
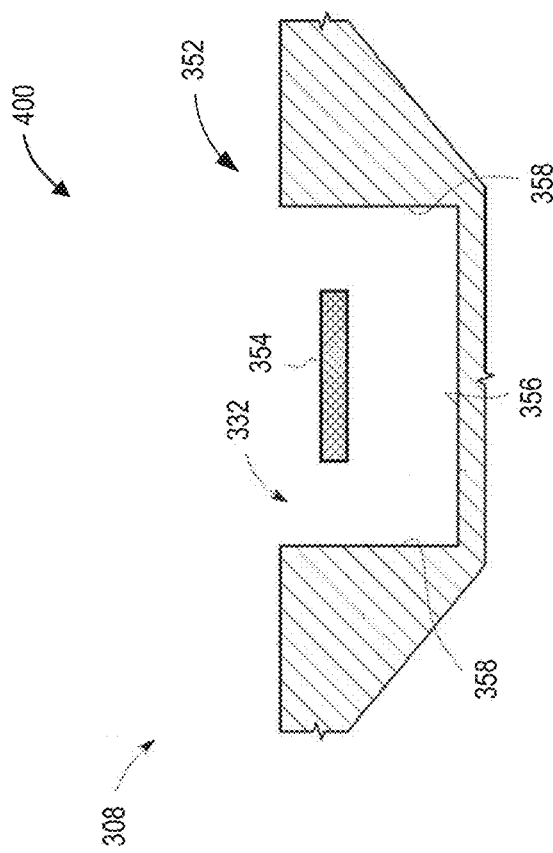
FIG. 4 is a cross-sectional view of a cathode cup according to one embodiment of the disclosure.
Figure 6:
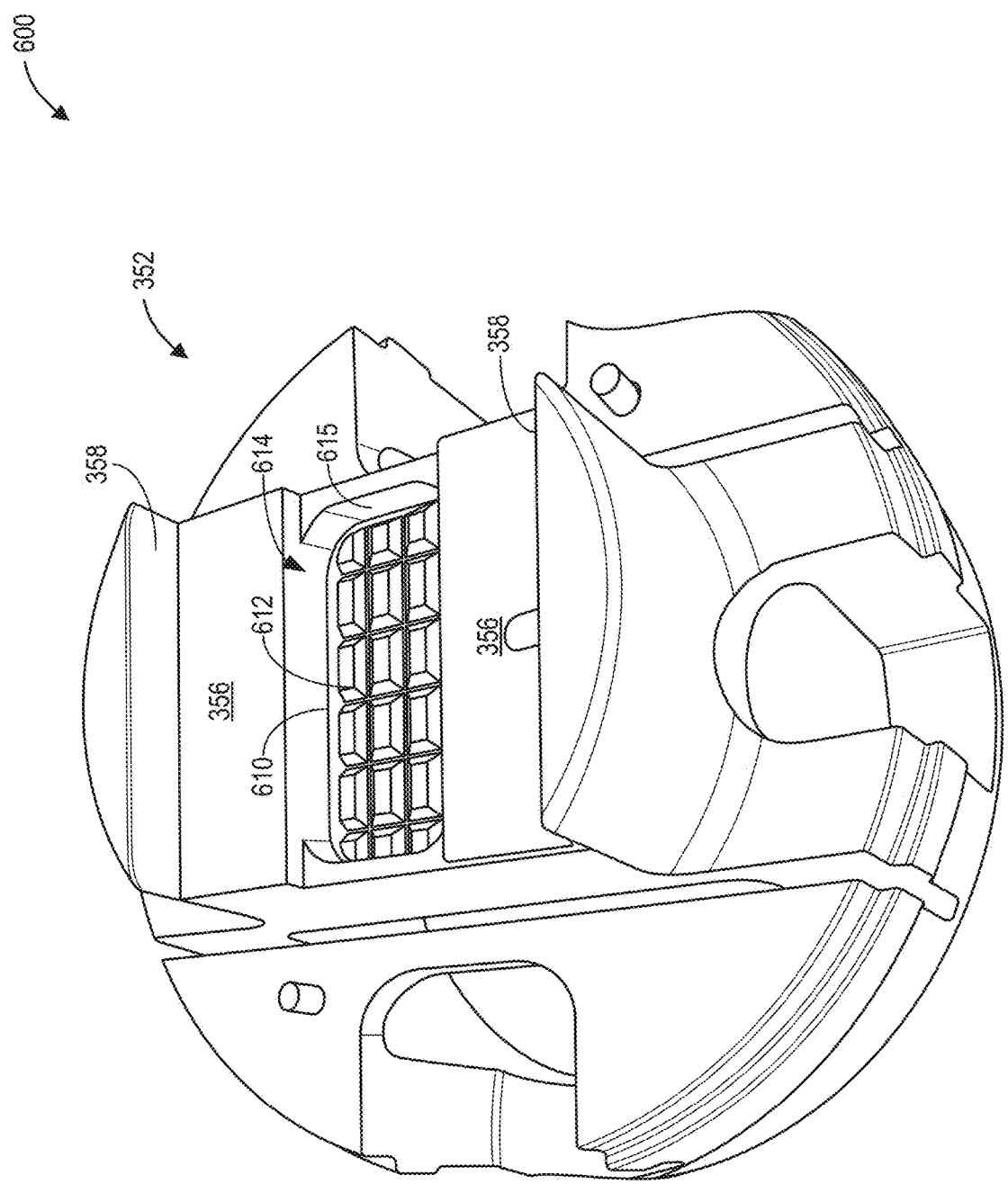
FIG. 6 shows a schematic of the cathode cup including a textured surface.

The following description relates to an x-ray system with a cathode cup having a surface finish to aid in adherence of deposited films. The following description relates to various embodiments of medical imaging systems that includes an x-ray system. An example of a CT imaging system that includes a cathode cup processed in accordance with the present techniques is provided in FIGS. 1 and 2. An x-ray source comprising an x-ray tube including a cathode cup and an emitter is shown in FIG. 3. An example cathode cup including an emitter is shown in FIGS. 4 and 5. The surface of the cathode cup facing the emitter may be textured to facilitate adherence of material that sublimate form the emitter during operation of the x-ray tube. A schematic of a cathode cup is shown in FIG. 6. A portion of the cathode cup may include a distinct pattern. In order to form a surface texture on the cathode cup, the cathode cup may be exposed to chemical etching or mechanical blasting processes, as elaborated in the example processes in FIGS. 11 and 12. In the chemical etching process, the degree of etching achieved to form a desired texture is based on an exposure time to the etchant used. FIGS. 7A-10 C shows microscopy images of portions of a cathode cup captured at different durations of exposure of the cathode cup to the chemical etchant.

Though a CT imaging system is described by way of example, it should be understood that the present techniques may also be useful for manufacturing components in other x-ray imaging systems, such as x-ray tomosynthesis imaging systems, mammography imaging systems, C-arm imaging systems, interventional imaging systems, radiography imaging systems, fluoroscopy imaging systems, and so forth. The present discussion of a CT apparatus is provided merely as an example of one suitable imaging technique using radiation shields manufactured via mentioned methods.

During operation of the x-ray tube often at elevated temperatures of around 2000° C., sublimated or evaporated emitter material may deposit onto colder surfaces of the cathode cup. Since the cathode cup is made from a different alloy than the emitter material, there is a thermal expansion mismatch between the deposited material and the material of the cathode cup. For example, cathode cups may be typically made of nickel, molybdenum, Fe-41.5Ni (Ni42), Fe-29Ni-17Co (Kovar), or niobium while the deposited emitter material may often be comprised of tungsten.

Due to high temperature fluctuation that occurs during the x-ray exposure, which may be 400° C. or more at the surface of the cathode cup, the differences in the coefficient of thermal expansion (CTE) of the cathode cup and the deposited emitter material may cause unequal thermal expansion of the cathode cup material and the deposited material. Thermo-mechanical stress due to different thermal expansion coefficients may cause deposited emitter material to shear off of the surface of the cathode cup and become loose within the area below the emitter, and between a side of the emitter and a surface of the cathode cup. This separation may start at the borders of the deposited emitter material or at areas of uneven deposition.

A need for an improved cathode cup that better adheres sublimated emitter material away from the electron emitter so as to reduce the possibility of emitter failure due to shorts caused by loose or flaking sublimated emitter material is recognized. It is desired that the cathode cup provides improved high voltage stability by reducing possibility of loose sublimated emitter material in the high voltage gap between the emitter and the cathode cup.

For example, one prior art solution included creating a cavity beneath the emitter to assist in adhesion between the deposited emitter material and the bottom surface of the cup. However, the inventors have recognized that this solution alone is insufficient to inhibit the deposited emitter material to become loose. Due to thermal expansion differences, such as differences in CTE between the deposited emitter material and the cathode, the unmodified surface finish of the cavity would still incur undesired flaking since the features of the cavity may be insufficient to maintain a mechanical adherence of the deposition.

In one example, the issues described above may be addressed by developing the disclosed cathode cup which comprises a recessed cavity of the cathode cup being microscopically textured. The texturing may be done mechanically by physical etching with fine media for use in blasting or equivalent. The texturing may also be done chemically etching. Chemical etching etches features of the microstructure creating an irregular texture aiding adhesion of deposited emitter films.

In this way, by forming a microstructure on the surface with features that allow capture of sublimated emitter material, the deposited material may be retained on the cathode cup for a longer duration without peeling off. The technical effect of the disclosed texturing reduces emitter degradation caused by flaking layers of material coming in contact with the emitter. The additional texturing in the microscope scale extends the time duration before the onset of deposited emitter material spalling off. Overall, the disclosed textured cathode cup extends the lifetime of the emitter over existing cathode cup embodiments.

Figure 1:
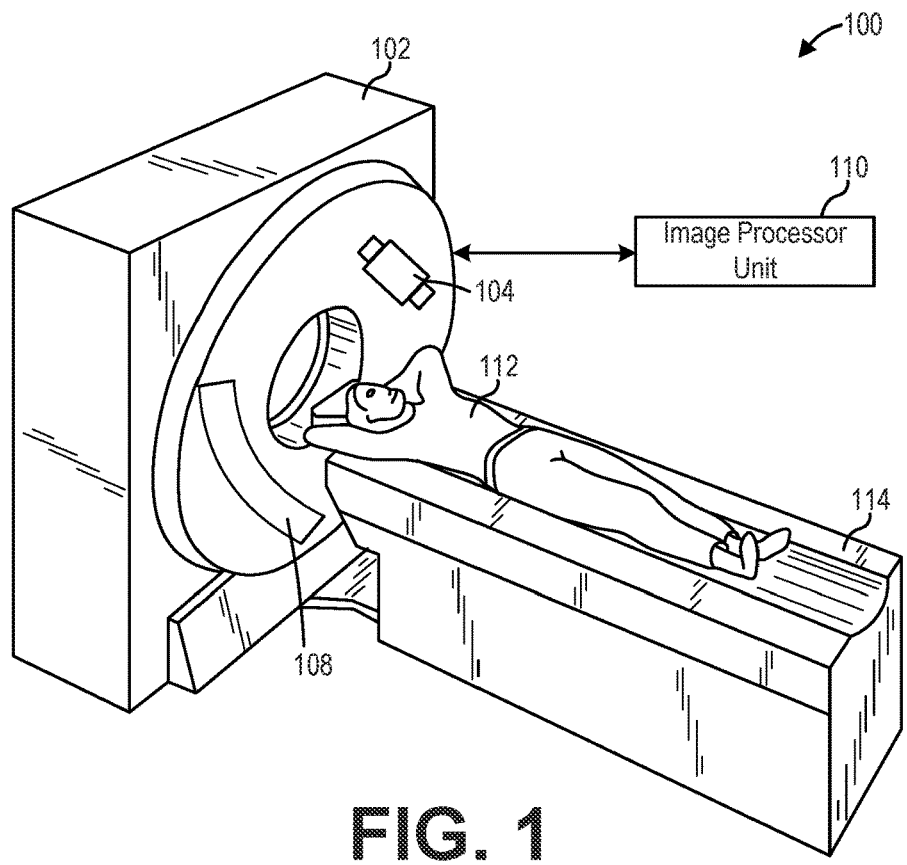
FIG. 1 shows a pictorial view of an imaging system according to an embodiment.

FIG. 1 illustrates an exemplary CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation 106 (see FIG. 2) for use in imaging the subject 112 laying on a table 114. Specifically, the x-ray source 104 is configured to project the x-ray radiation beams 106 towards a detector array 108 positioned on the opposite side of the gantry 102. Although FIG. 1 depicts only a single x-ray source 104, in certain embodiments, multiple x-ray sources and detectors may be employed to project a plurality of x-ray radiation beams 106 for acquiring projection data at different energy levels corresponding to the patient. In some embodiments, the x-ray source 104 may enable dual-energy gemstone spectral imaging (GSI) by rapid peak kilo voltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of a radiation beam by the object. Each detector element of the array produces a separate electrical signal that is a measurement of the x-ray beam attenuation at the detector location. The attenuation measurements from all the detector elements are acquired separately to produce a transmission profile.

In some CT systems, the x-ray source and the detector array are rotated with a gantry within the imaging plane and around the object to be imaged such that an angle at which the radiation beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

Figure 2:
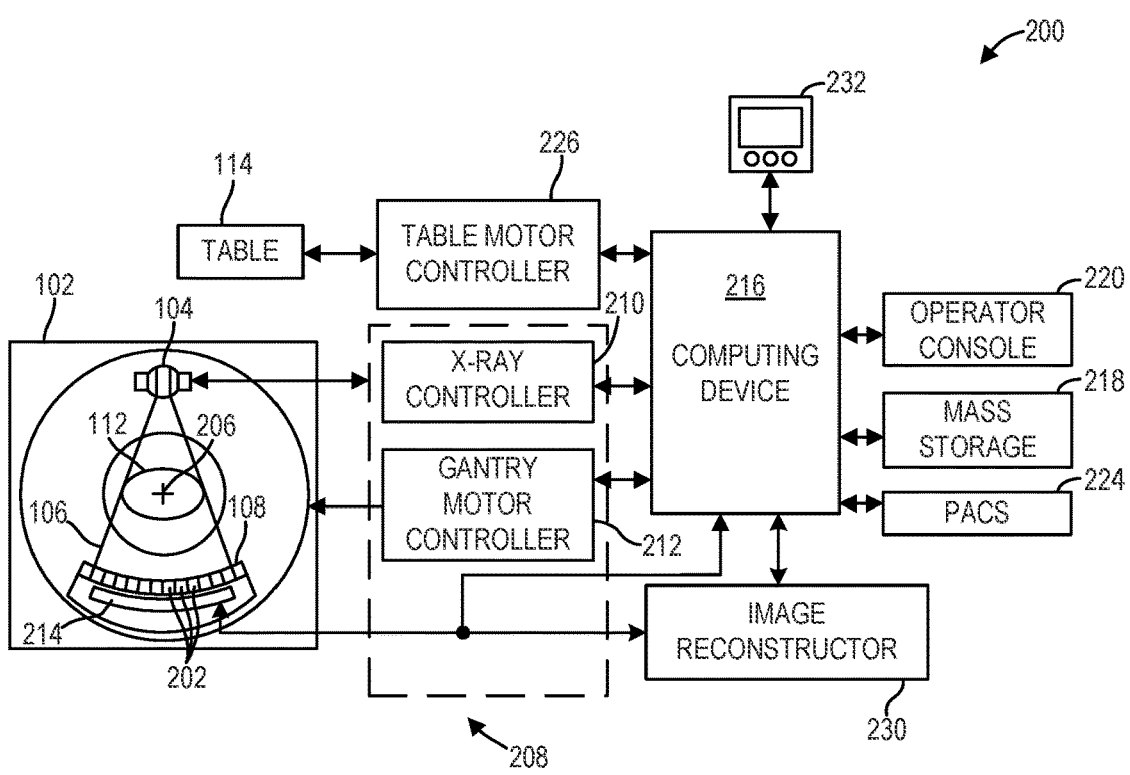
FIG. 2 shows a block schematic diagram of an exemplary imaging system according to an embodiment.

FIG. 2 illustrates an exemplary imaging system 200 similar to the CT system 100 of FIG. 1. In accordance with aspects of the present disclosure, the imaging system 200 is configured for imaging a subject (e.g., the subject 112 of FIG. 1). In one embodiment, the imaging system 200 includes the detector array 108 (see FIG. 1). The detector array 108 further includes a plurality of detector elements 202 that together sense the x-ray radiation beam 106 (see FIG. 2) that pass through the subject 112 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods and processes described further herein may be stored as executable instructions in non-transitory memory on a computing device (or controller) in imaging system 200. In one embodiment, image reconstructor 230 may include such executable instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

FIG. 3 illustrates an example x-ray source used in the imaging system of FIG. 1. In one example, x-ray source 300 may be the x-ray source 105 in FIG. 1. The x-ray source may include an x-ray tube 302 wherein an x-ray beam is generated and a collimator 304 wherein the x-ray beam is collimated to a desired beam size.

The x-ray tube 302 may include a cathode 308 and an anode 306 (also referred herein as target) positioned opposite to one another enclosed within a vacuum vessel 305. The anode 306 may be rotated about a longitudinal axis of a pillar 315 supporting the anode 306. The cathode 308 may include a cathode cup 352 enclosing an emitter 354. A high voltage electrical circuit may be electrically coupled to the x-ray tube 302 and configured to supply power to the x-ray tube 302.

In one example, the high voltage electrical circuit may include a cathode multiplier electrically coupled to a high voltage transformer and the cathode 308, and an anode multiplier electrically coupled to the high voltage transformer and the anode 306. The cathode multiplier may be configured to supply a negative high voltage DC to the cathode 308, for example via high voltage connection, while the anode multiplier may be configured to supply a positive high voltage DC to the anode 306, for example via high voltage connection. That is, the cathode 308 and the anode 306 may carry equal voltages of different polarity. In this way, a high voltage potential difference between the cathode 308 and the anode 206 may be generated.

The power supplied to the x-ray tube 302 may create the potential difference of, for example, 60 kV to 140 kV between the emitter 354 of the cathode 308 and the anode 306, thereby causing electrons generated by the emitter 354 to accelerate towards the anode 306. As the electrons collide with the anode 306 at a high velocity, at least a portion of the kinetic energy of the electrons is converted to high frequency electromagnetic radiation, or x-rays 310.

In one example, the cathode cup 352 may be made of nickel, molybdenum, Fe-41.5Ni (Ni42), Fe-29Ni-17Co (Kovar), or niobium, the emitter 354 may be made of tungsten, and the anode may be made 306 may be made of tungsten or molybdenum. The cathode cup 352 may include inner side walls 358 and inner base 356 (also referred to herein as inner bottom surface 356 or simply, bottom surface 356) directly facing the emitter 354. Specifically, the inner base 356 has a line of sight to the emitter 354. Due to high temperature of the emitter 354, material from the emitter may vaporize and sublimate and then deposit on the side walls 358 and base 356 of the cathode cup facing the emitter 354. In order to entrap and retain the emitter material on the cathode cup without flaking, the surface of the cathode cup facing the emitter 354 may be sculpted to form microstructures.

The material forming the surface of the cathode cup 352 may be made up of many crystals of various individual orientations. These individual crystals may be termed as "grains." In any one grain, all atoms may be arranged with one particular orientation and one particular pattern. The juncture between adjacent grains may be termed as "grain boundary." The grain boundary is a transition region in which some atoms are not entirely aligned with either grain. The mismatch of the orientation of neighboring grains leads to a less efficient atomic packing within the grain boundary. Hence the atoms in the boundary have a less ordered structure and a slightly higher internal energy. The grain-boundary atoms may be more easily and rapidly dissolved or "corroded" using chemical and/or mechanical texturing methods than the atoms within the grains.

The surface (such as side walls 358 and base 356) of the cathode cup 352 facing the emitter 354 may be chemically and/or mechanically textured to include a plurality of etched features with grains boundaries of the material having a higher than threshold depth of 10 µm to entrap sublimated material from the emitter. The chemically texturing includes chemically etching the surface such as by dispensing an amount of a chemical etchant onto the surface and exposing the surface to the chemical etchant for a higher than threshold duration. The amount of the chemical etchant dispensed on the surface may be directly proportional to a level of texturing to be attained on the surface, the amount of chemical etchant increasing with the level of texturing. The level of texturing may include a distance between two adjacent features (that is, distance between two adjoining features) and a depth of each feature, the level of texturing increasing with each of a decrease in the distance between two adjacent features and an increase in the depth of each feature. The threshold depth of each feature may be 10 µm. In some examples, the threshold depth of each feature may be in a range of 1 µm and 10 µm.

The mechanical texturing may include blasting the surface with a coarse medium for another threshold duration. The blasting may include propelling the coarse medium on the surface from a dispenser at an elevated pressure for the another threshold duration. Each of the threshold duration of exposure of the surface to the chemical etchant and the another threshold duration of blasting may be based on the level of texturing to be attained on the surface.

Each feature on the textured surface of the cathode cup may be a grain of a material constituting the surface, the depth of each feature being a depth of a grain boundary and the distance between two adjacent features being a distance between two adjacent grain boundaries. The depth of each feature is in a range of 10 µm and 1000 µm, and wherein the distance between two adjacent features is in a range of 100 nm and 1000 µm. In one example, the depth of each feature is in a range of 10 µm and 200 µm; and the distance between two adjacent features is in a range of 100 nm and 200 µm. In some examples, such as when heat treatment is employed, a grain coarseness may increase, and as such, the depth of each feature may be in a range of 10 µm and 10 mm, and the distance between adjacent features may be in a range of 100 nm and 10 mm. Further, the depth and the distance may be dependent on an initial grain coarseness prior to etching, the initial grain coarseness including an initial grain depth and an initial distance between two adjacent grains.

The x-ray tube 302 may be enclosed in a vacuum vessel 305 including a transmissive port 344. As an example, the vessel 305 may include a first radiation shield 330 arranged to block x-rays traveling in undesirable directions. The radiation shield may enclose the entire x-ray tube except for the transmissive port 344. The radiation source may further include a collimator 204 adjoining the x-ray tube. The x-rays 310 exiting the x-ray tube 202 via the transmissive port 344 may enter the collimator. The collimator may include a first collimator blade 318 and a second collimator blade 320 positioned coaxially along a longitudinal axis A-A'. The distance between the first collimator blade 318 and the second collimator blade 320 may be adjusted to form an opening or aperture 324. The first collimator blade 318 and the second collimator blade 320 may be moved relative to each other along the A-A' axis to adjust the aperture 324 size. The collimator 304 may be enclosed in a second radiation shield 322 except for a port 316. A portion of the x-rays 310 may pass through the opening or aperture 324 between the first collimator blade 318 and the second collimator blade 220 and the transmitted x-ray beam 314 may exit the collimator via the port 316. A portion of the x-rays impinging on the first collimator blade 318 or the second collimator blade 320 may be reflected from the respective blade and the reflected x-rays 312 may be absorbed by the second radiation shield 322. In this way, the reflected rays from the collimator blades are restricted from exiting the collimator.

The x-ray beam 314 exiting the collimator 304 may then be directed to penetrate an object (not shown), such as human anatomical parts for medical examination and diagnostic procedures. The x-rays transmitted through the object are intercepted by a detector (not shown) and an image is formed of the internal anatomy. Further, industrial x-ray tubes may be used, for example, to inspect metal parts for cracks or to inspect the contents of luggage at airports.

FIG. 4 depicts a cross-section 400 of an exemplary cathode 308 of an x-ray system. The cathode 308 comprises an emitter 354 and a cathode cup 352 that holds the emitter 354. In some examples, the emitter 354 may be coupled to a surface (such as a bottom surface 356) of the cathode cup 352 via one or more support arms (not shown). The cathode cup may be made of any material, such as nickel, molybdenum, Ni42, Kovar, or niobium. The emitter 354 is positioned within the recess 332 such that the cathode cup 352 acts as an electron focusing element to guide electrons from the emitter 354 towards an anode. In various embodiments, the emitter 354 may be a plate, a coil, a filament, or other type of emitting device known in the relevant art. The emitter 354 may be parallel to the bottom surface 356 of the recessed cavity 332 or may be angled at any angle with respect to the bottom surface 356.

The recessed cavity 332 is formed in the material of the cathode cup 352. The cathode cup 352 includes inner bottom surface 356 that faces the emitter 354 (that is, the bottom surface 356 has a line of sight to the emitter 354). The cathode cup 352 may have one or more sidewalls 358, which may be perpendicular to the bottom surface 356, or at any angle thereto. Alternatively, the cathode cup 352 may be bowl-shaped or otherwise have a curved bottom surface 356.

FIG. 5 shows an isometric view 500 of a texture on a cathode cup 352. The texturing may be applied to the bottom surface 356 and side surfaces 358 of the cathode cup 352. The texturing is meant for all surfaces that may have deposited emitter material resulting from sublimation of the emitter material during the high voltage exposure and electron emission at the emitter 354. As an example, the sidewalls 358 and the bottom surface 356 of the cathode cup 352 may be textured. In various embodiments, the recessed cavity microscopic texturing may be done by mechanical or chemical methods. The texturing, at the microscopic level, allows emitter material to be deposited and retained on the surface of the cathode cup.

FIG. 6 shows a schematic 600 of the cathode cup 352 including a textured surface. The cathode cup 352 may include a patterned portion set within a cavity formed within the cathode cup 352. The cathode cup 352 may include sidewalls 358 on each side of the bottom surface 356. The bottom surface 356 may include a cavity 614 with a patterned surface 610. In this example, the cavity may be rectangular with non-patterned walls 615 on each side of the patterned surface 610. The patterned surface 610 may include a plurality of protrusions 612 forming a pattern. In this example, each protrusion 612 may be rectangular. Each protrusion 612 may include a flat upper surface with angled walls attached to the patterned surface 610. In one example, each protrusion may be identical in size and shape. In another example, there may be differences among the protrusion. The protrusions may cover the entire patterned surface 610 within the cavity formed on the bottom surface 356 of the cathode cup 352. The patterns break up flat surfaces of the cathode cup, and reduce flaking of the deposited emitter material.

In one example, the patterns may be formed by an end milling process. Other process such as electrical discharge milling (EDM), plunge EDM, knurling, etc., may be utilized to form the patterns and are within the scope of the disclosure.

The bottom surface 356 of the cathode cup including the patterned surface 610 may face the emitter. During operation of the x-ray tube, due to high temperature of operation, material from the emitter may sublime and deposit on surfaces of the cathode cup including the bottom surface 356, the patterned surface 610, the sidewalls 358 and other surfaces (such as walls 615) of the cavity 614. In order to retain the deposited material on the surface of the cathode cup, the surfaces exposed to the emitter material may be sculpted to form microstructures. Said another way, the surfaces of the cathode cup that receive the sublimated emitter material, including the bottom surface 356, the patterned surface 610, the side walls 358, and other surfaces of the cavity, may be etched to form microstructures (the plurality of features) having depth, and having spacing between adjacent microstructures. The microstructures facilitate mechanical adhesion of the deposited material on the surface even during temperature cycles, thereby reducing the possibility of the material flaking off of the surface and disrupting operation of the cathode cup. The microscopic texturing of the cathode cup surface may extend the time duration before an onset of deposited emitter material spalling off.

Since the different surfaces of the cathode cup may exposed to different levels of emitter material deposition, as an example, the level of microscopic texturing carried out on different surfaces of the cathode cup may vary. In one example, due to the higher exposure of the bottom surface 356 including the patterned surface 610 relative to that of the sidewalls 358 of the cathode cup, an increased level of texturing may be imparted onto the bottom surface 356 including the patterned surface 610 relative to that of the sidewalls 358. Methods of texturing the surface of the cathode cup via chemical etching and mechanical blasting are elaborated with relation to FIGS. 11 and 12.

Figure 11:
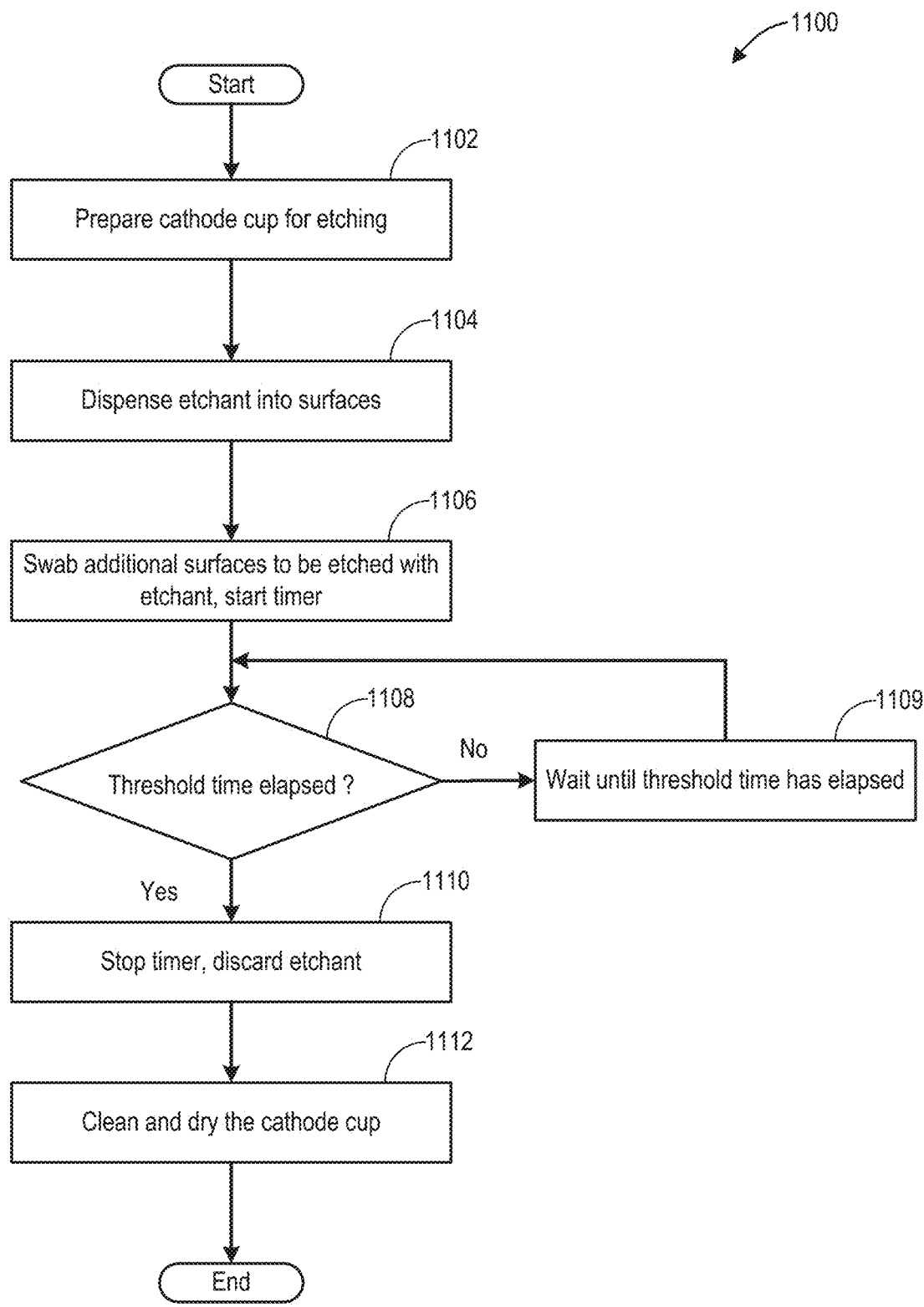
FIG. 11 shows a flow chart of an example method for texturing a cathode cup via chemical etching.

FIG. 11 shows an example method 1100 for texturing a cathode cup (such as cathode cup 352 in FIG. 6) via chemical etching. In particular, etching may be utilized preferentially attack grains, grains boundaries, or specific phases, thereby creating a roughening affect. One or more surfaces of a cathode cup exposed to deposits from an emitter may be textured at a microscopic level. The surfaces of the cathode cup that are textured may include the bottom surface (such as bottom surface 356 in FIG. 6), the sidewalls (such as sidewalls 358 in FIG. 6), and the patterned surface (such as surface 610 in FIG. 6) including the protrusions on the cathode cup.

At 1102, the surfaces of cathode cup may be prepared for etching. Preparing the surfaces for etching may include cleaning the surfaces. Preparing the surfaces may further include masking selected regions for which texturing is not desired. As an example, a masking material fabricated from a material resistant to the etchant selected may be applied to the selected regions to protect selected regions from the etchant.

At 1104, an etchant chemical may be dispensed onto the surfaces to be etched. Specifically, the etchant chemical is selected to preferentially etch, grains, grain boundaries, and/or specific phases. The etchant may be added using a pipette, a syringe, a dropper, or a similar dispenser. The etchant may be liquid chemical which may completely cover the surface to be textured. Example chemical etchants may be acids or bases. Example acid compounds include hydrofluoric acid (HF), sulfuric acid ($H_2SO_4$), nitric acid ($HNO_3$), hydrochloric acid (HCl), ferric chloride, or any combination thereof. Example base compounds that may be used for chemical etching include sodium hydroxide (NaOH), potassium hydroxide (KOH), ammonium hydroxide ($NH_4OH$) or any combination thereof. Texturing the surface includes etching away material from the grain boundary to increase the roughness of the surface. A degree of texturing may be based on size of features such as grains on the material on the surface. In particular, the degree of texturing may be based on an initial depth of a feature, and an initial spacing between two adjacent features (prior to etching).

In one example, after etching, the distance between features may be in a range of 100 nm and 10 mm, and the depth of the features may be in a range of 10 μm and 10 mm. In another example, after etching, the distance between features may be in a range of 100 nm and 1000 μm, and the depth of the features may be in a range of 10 μm and 1000 μm. In yet another example, after etching, the distance between features may be in a range of 100 nm and 200 μm, and the depth of the features may be in the range of 10 μm and 200 μm. It will be appreciated that the depth of a feature and the distance between adjacent features may vary proportionally depending on the type of treatment and initial coarseness of the features.

A distance between features may be a distance between two adjacent grain boundaries. As an example, a first level of texturing may include the distance between features in the range of 100 nm and 2 µm, and the depth of the features be in the range of 10 µm and 20 µm. As another example, a second level of texturing may include the distance between features in the range of 2 µm and 200 µm, and the depth of the features in the range of 20 µm and 200 µm. The first, higher degree of texturing may be applied to surfaces directly facing the emitter (higher exposure to sublimate from emitter) such as bottom surface including the patterned surface of the cathode cup. The second, lower degree of texturing may be applied to surfaces not directly facing the emitter (lower exposure to sublimate from emitter) such as sidewalls of the cathode cup.

The concentration and/or a contact duration of the etchant dispensed on the surface may be proportional to the degree of texturing desired to be attained on that surface. In one example, for surfaces to be textured with the first, higher level of texturing (that is, with increased depth of the features and/or increased spacing between the features), a first, higher concentration of etchant may be dispensed on the surface. In another example, for surfaces to be textured with the second, lower level of texturing (that is, with reduced depth of the features and/or reduced spacing between the features), a second, lower concentration of etchant may be dispensed on the surface. Additionally or alternatively, contact durations of the etchants may be changed to achieve the desired degree of texturing. For example, contact duration of the etchant may be increased to increase the degree of texturing, and vice-versa.

At 1106, additional surfaces which have not been covered with the etchant chemical may be swabbed with the etchant chemical. The etchant chemical may be dabbed in an applicator such as a swab and lathered on the surfaces to be etched. Once each of the surfaces to be textured have been covered with the chemical etchant, a timer may be started. Chemical reaction between the etchant and the material of the surface causes the material to be removed along the grain boundaries, thereby accentuating grain boundaries and creating textures of an intended feature size.

At 1108, the routine includes determining if a threshold time has elapsed since the deposition of the chemical etchant on the surfaces. As time progresses, the etching action takes place. The threshold duration of the etching may be pre-calibrated based on the level of texturing desired on the surfaces being etched and the type of chemical used. As an example, the threshold duration may be increased if a higher level of texturing is desired. If it is determined that the threshold time has not elapsed since the deposition of the chemical etchant on the surfaces, at 1109, the routine may wait until the threshold time has elapsed. It may be inferred that the desired level of texturing has not yet been attained and further time is desired or continuation of the chemical reactions causing etching.

If it is determined that the threshold time has elapsed since the deposition of the chemical etchant on the surfaces, it may be inferred that the desired level of etching has been attained. At 1110, the timer may be stopped and the remaining etchant chemical may be discarded. Discarding the etchant may include wiping the surface, neutralizing, and/or removing the chemical with an appropriate solution depending on the etchant chemical used.

At 1112, the surface of the cathode cup that is textured may be cleaned with water/cleaning solution and then the surface may be dried at room temperature to remove all traces of water/solution.

Once the texturing is completed, the surface may be characterized. The surface topology (quantification of surface roughness) of the surface may be determined via a surface measuring instrument. In one example, a standard optical profilometer, such as an interferometer, may be used to determine the surface roughness. In this non-contact profilometry method, the surface is scanned with a beam of light and the reflection of the beam from the surface is quantified to determine the roughness of the surface. As an example, a depth of features (surface textures) may be estimated to be around 10 µm with a deviation of ±3 µm.

Figure 7B:
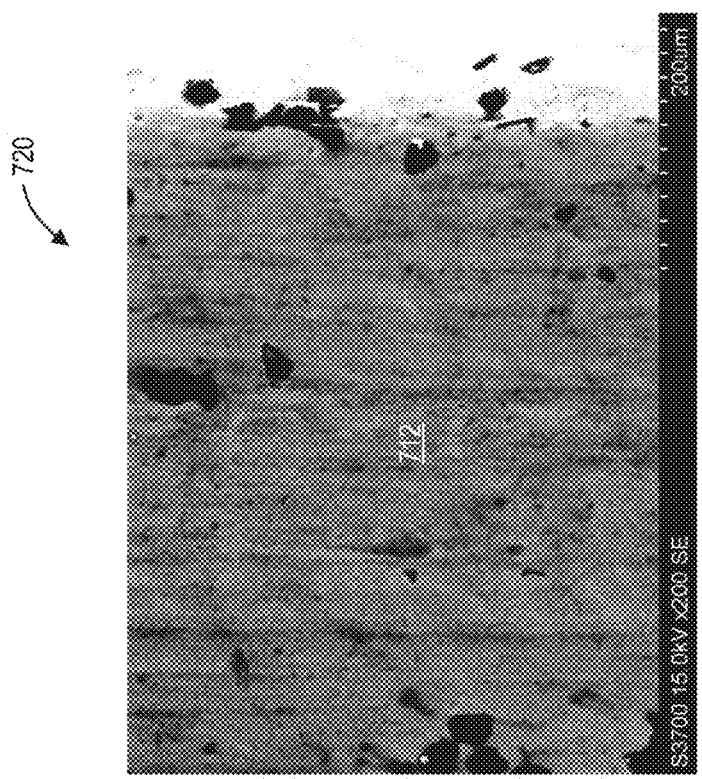
FIG. 7B shows a second microscopic image of the cathode cup surface prior to texturing.
Figure 7A:
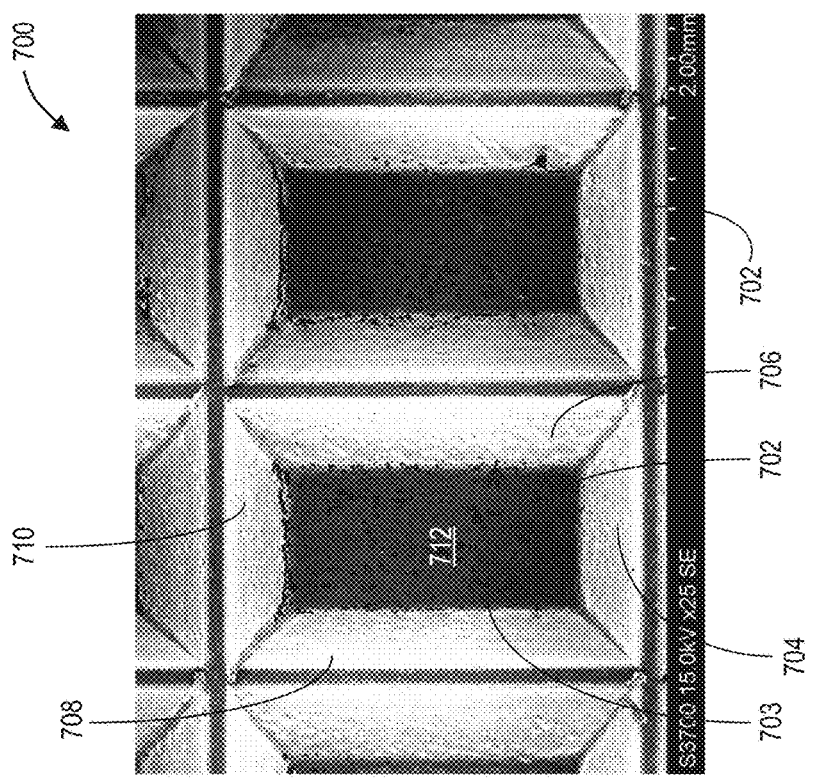
FIG. 7A shows a first microscopic image of a cathode cup surface prior to texturing.

In order to further determine the texture of the surface, the surface of the cathode cup may be inspected via optical and electron microscopy before and after the texturing is being carried out. FIG. 7A-7B shows microscopic images of a cathode cup surface prior to texturing. The cathode cup surface being imaged may be the patterned surface (such as surface 610 in FIG. 6) including the protrusions on the cathode cup.

The first image 700 in FIG. 7A may be captured via scanning electron microscopy (SEM). The patterned surface 702 may be the patterned surface 610 in FIG. 6 which may include a plurality of repeated, symmetric protrusion 703 forming a pattern. In this example, each protrusion 703 is a tapering rectangular protrusion. Each protrusion 703 may include a wider base and a narrower top surface such as a flat rectangular upper surface 712 with angled walls on each side attached to a base of the patterned surface 702. The walls may include two longer side walls 706 and 708 and two shorter side walls 704 and 710 bordering the flat upper surface 712. As seen from this image, the shorter side walls 704 and 710 may be about 2 µm (with a 10% error margin) long at the base while the longer side walls 706 and 708 may be about 2.5 µm long at the base (where the wall meets the surface 702).

The upper flat surface 712 of one of the protrusions is magnified in the second SEM image 720 in FIG. 7B. In this image, it is seen that the surface 712 is largely smooth without any significant textures/patterns/undulations/microstructures. Even if sublimated material from the emitter is deposited and captured in a protrusion, due to the smooth upper surface of the protrusion, the deposited material may flake away. A mismatch in thermal expansion between the surface and the deposited material may cause the deposited material to be easier removed from the smooth surface. As previously elaborated, in order to retain the deposited material on the surface of the cathode cup longer, the surfaces of the cathode cup facing the emitter may be textured.

Figure 8B:
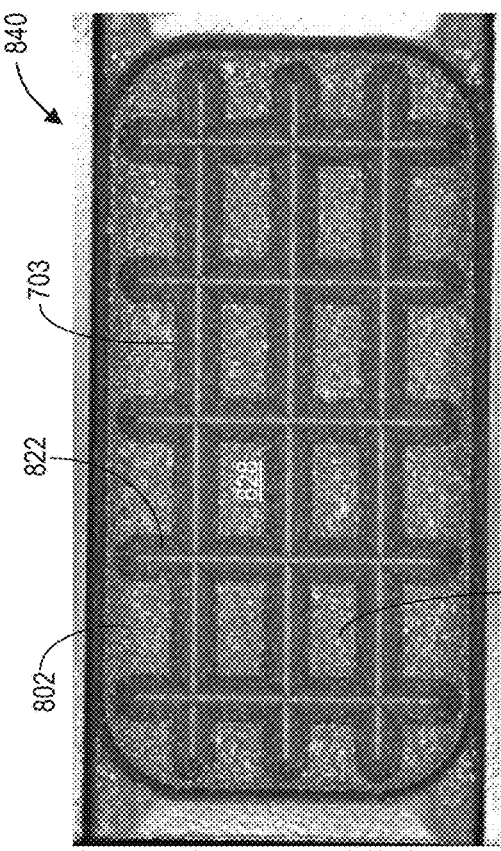
FIG. 8B shows a second optical microscopy image of the portion of the cathode cup exposed to a second duration of chemical etching.
Figure 8A:
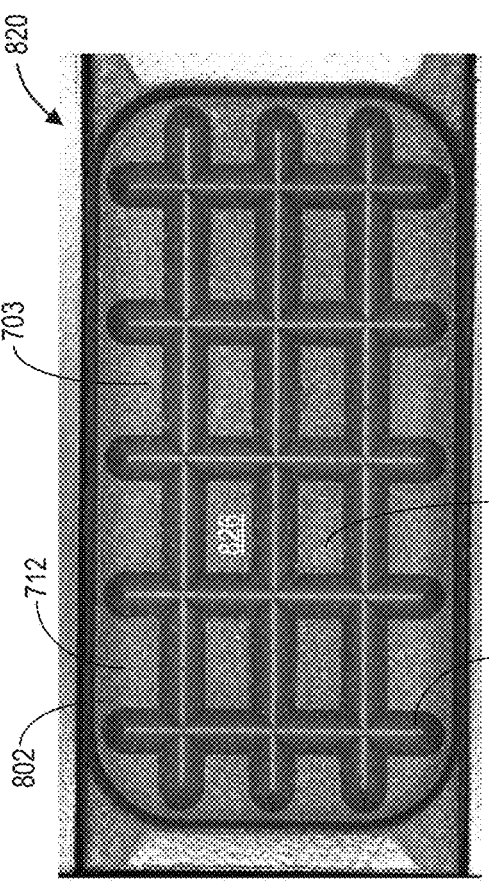
FIG. 8A shows a first optical microscopy image of a portion of the cathode cup with a first pattern exposed to a first duration of chemical etching.
Figure 8C:
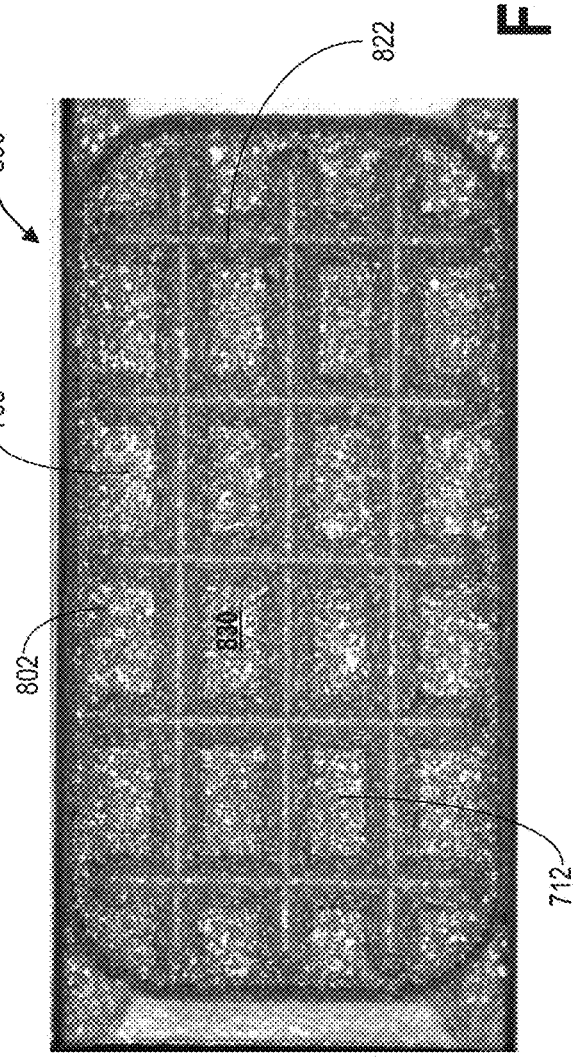
FIG. 8C shows a third optical microscopy image of the portion of the cathode cup exposed to a third duration of chemical etching.
Figure 9B:
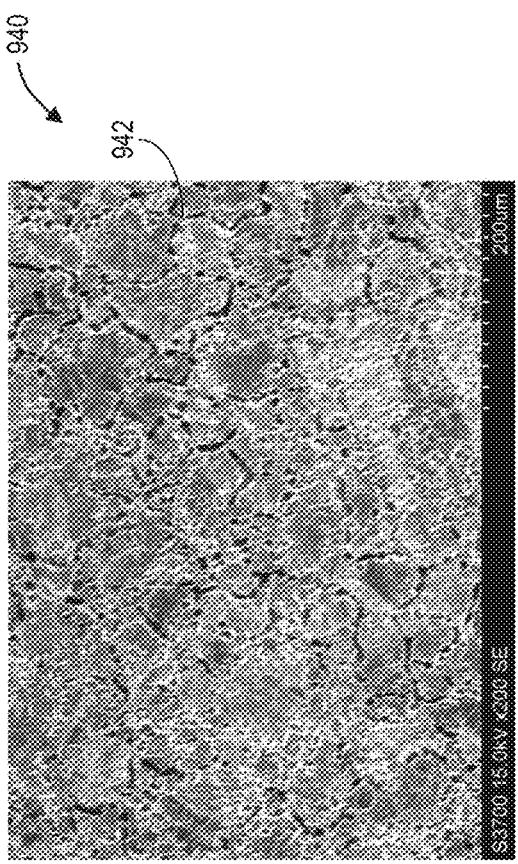
FIG. 9B shows a second electron microscopy image of the portion of the cathode cup exposed to the second duration of chemical etching.

During etching, the change in the surface of the cathode being etched may be imaged at different stages of the etching process. FIGS. 8A-C show optical microscopy images of a surface of the cathode cup with a first pattern exposed to a first, second, and third durations of chemical etching, receptively. FIGS. 9A-C show SEM images of a surface of the cathode cup with the first pattern exposed to the first, second, and third durations of chemical etching, receptively.

FIG. 8A shows a first optical microscopy image 820 of a surface 802 of the cathode cup with a first pattern exposed to a first duration of chemical etching. The surface 802 imaged may be the patterned surface 702 in FIG. 7A. The patterned surface 802 may include plurality of repeated, symmetric protrusions 703 forming a pattern. Each protrusion 703 may include a flat rectangular upper surface 712 with angled walls 822. The pattern may include flat elevated surfaces 712 separated by walls 822 forming a cheered pattern. During chemical etching, the entire surface 802 may be covered with a chemical etchant and the etchant may be allowed to react to the surface for a pre-calibrated duration forming a desired pattern. In this example, the surface has been exposed to a chemical etchant such as ferric chloride for 5 minutes (first duration).

FIG. 9A shows a first scanning electron microscopy image 920 of the surface 802 of the cathode cup with the first pattern exposed to the first duration of chemical etching. As an example, a flat, elevated, surface 826 of one of the protrusions 703 as seen in image 820 may be magnified in the image 920. As seen from images 820 and 920, due to the etching on the surface, textures (such as lines 922) are visible as lines on the surface. The material at the grain boundaries of the material of the surface are etched away (eroded) to form a rough surface. The lines 922 may denote amplified grain boundaries. The texture may constitute a series of crests and troughs along the grain boundaries. The width of the lines 922 may denote the level of amplification of the grain boundaries attained by the etching process. As the etching continues, the lines 922 may broaden and newer features may be formed, thereby increasing the surface roughness.

FIG. 8B shows a second optical microscopy image 840 of a surface 802 of the cathode cup with a first pattern exposed to a second duration of chemical etching. The second duration may be longer than the first duration such that the image 840 of the same surface 820 may be captured after capturing the first optical microscopy image 820 (as the etching process progresses). As an example, the first duration of chemical etchant exposure may be 5 minutes and the second duration of chemical etchant exposure may be 10 minutes, the chemical etchant that the surface is exposed to being ferric chloride.

FIG. 9B shows a second scanning electron microscopy image 940 of the surface 802 of the cathode cup with the first pattern exposed to the second duration of chemical etching. As an example, a flat, elevated, surface 828 of one of the protrusions 703 as seen in image 840 may be magnified in the image 940. As seen from images 840 and 940, due to continued etching on the surface, textures (such as lines 942) become more prominent compared to that in image 920. The width of the lines 942 increase and the grain boundaries become visible, thereby increasing the level of surface texturing.

FIG. 8C shows a third optical microscopy image 860 of the surface 802 of the cathode cup with a first pattern exposed to a third duration of chemical etching. The third duration may be longer than each of the first duration and the second duration such that the image 860 of the same surface 820 may be captured after capturing each of the first optical microscopy image 820 and the second optical microscopy image 840 (as the etching process progresses). As an example, the first duration of chemical etchant exposure may be 5 minutes and the second duration of chemical etchant exposure may be 10 minutes, and the third duration of chemical etchant exposure may be 15 minutes, chemical etchant that the surface is exposed to being ferric chloride.

FIG. 9C shows a third scanning electron microscopy image 960 of the surface 802 of the cathode cup with the first pattern exposed to the third duration of chemical etching. As an example, a flat, elevated, surface 830 of one of the protrusions 703 as seen in image 860 may be magnified in the image 940. As seen from images 860 and 960, due to continued etching on the surface, textures (such as lines 922) become thicker and the grain boundaries become more prominent, thereby increasing the level of surface texturing. The grains are visible as features on the textured surface.

Figure 9D:
FIG. 9D shows a fourth electron microscopy image of the textured cathode cup showing distance between features.
Figure 9A:
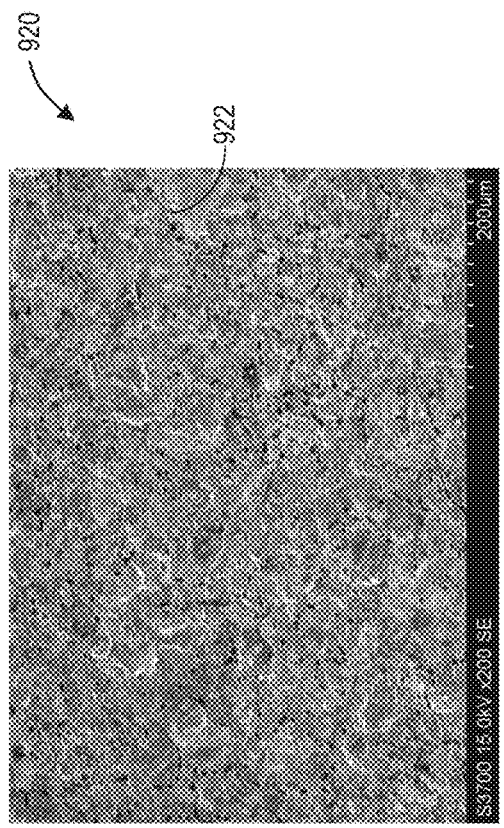
FIG. 9A shows a first electron microscopy image of the portion of the cathode cup exposed to the first duration of chemical etching.
Figure 9C:
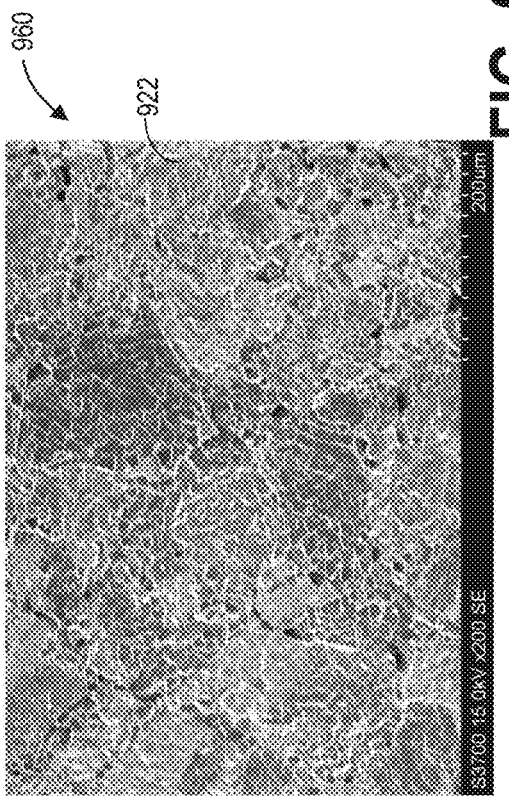
FIG. 9C shows a third electron microscopy image of the portion of the cathode cup exposed to the third duration of chemical etching.

FIG. 9D shows a fourth electron microscopy image 980 of the textured cathode cup showing distance between the enhanced features 984 captured after exposing the surface to the chemical etchant for at least the third duration. As seen from the microscopy images, after exposing the cathode cup surface to a chemical etchant for the third duration, a distance between features (such as adjacent grains) may be in the of range 100 nm and 200 µm. The grain boundaries may have a depth in the range of 10 µm and 200 µm. In this way, texturing may be enhanced at a microscopic level to form a surface capable of retaining sublimated material deposited on it.

Figure 10A:
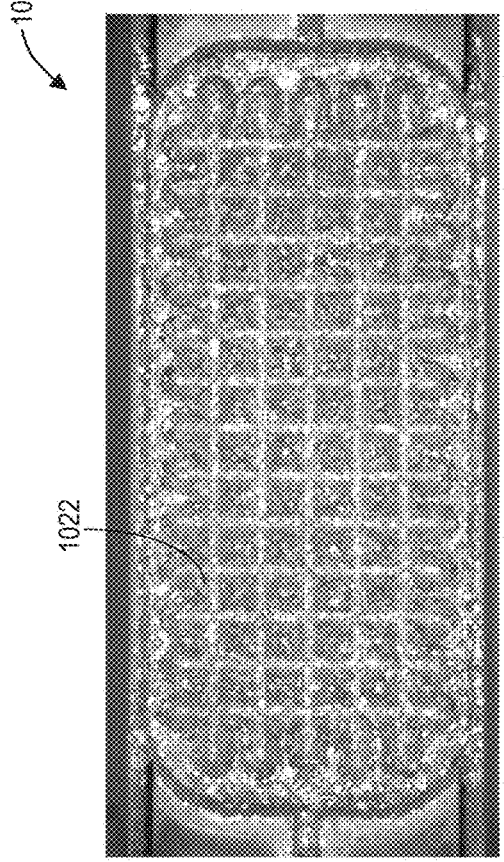
FIG. 10A shows a first microscopy image of a portion of the cathode cup with a second pattern exposed to a third duration of chemical etching.
Figure 10B:
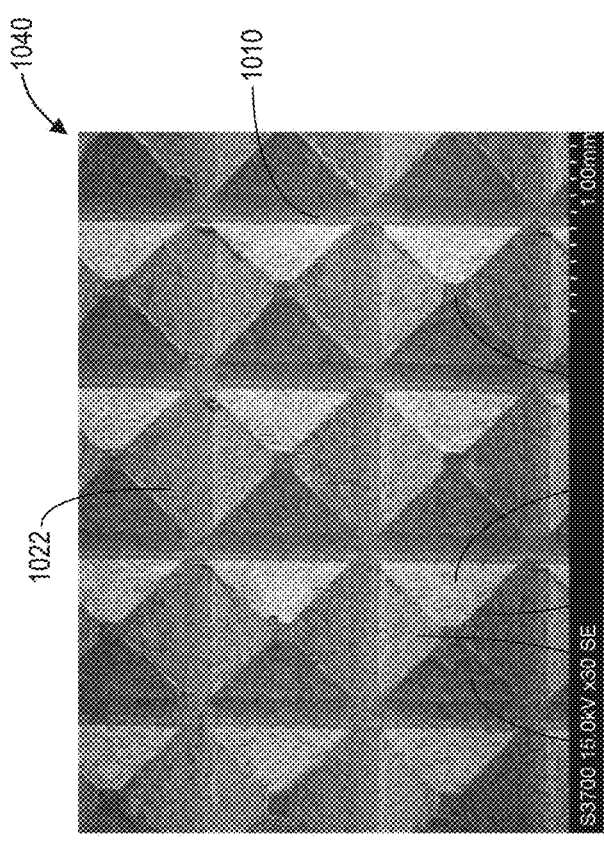
FIG. 10B shows a second microscopy image of a portion of the cathode cup with the second pattern exposed to the third duration of chemical etching.
Figure 10C:
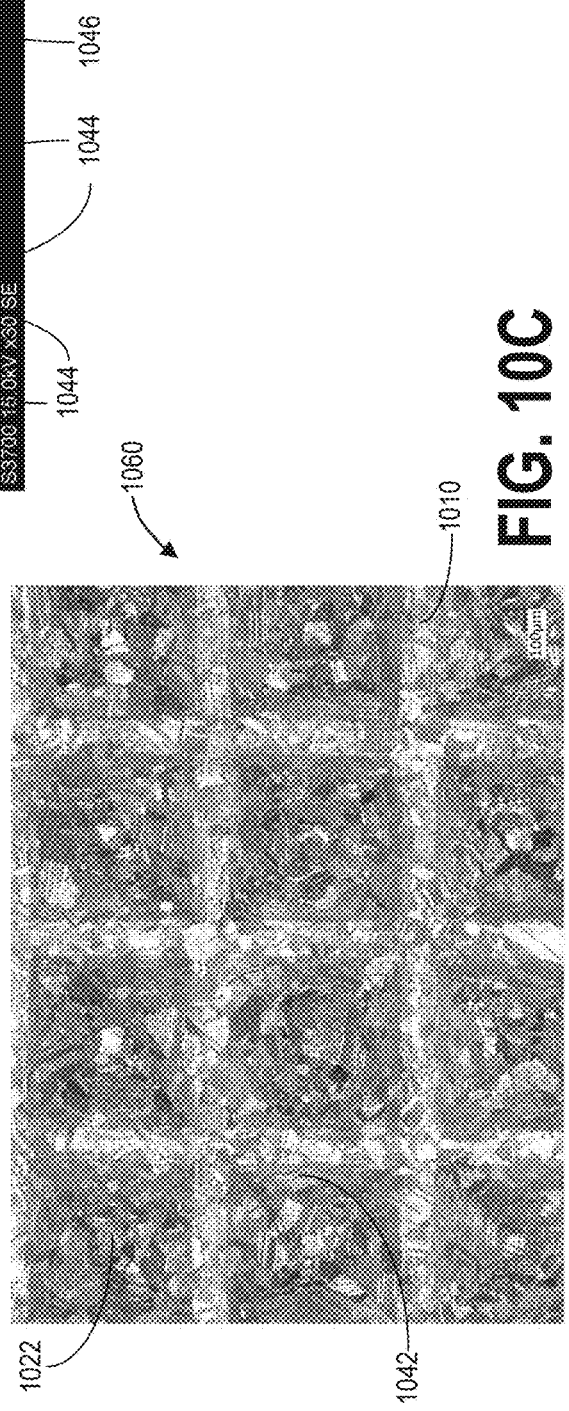
FIG. 10C shows a third microscopy image of a portion of the cathode cup with the second pattern exposed to the third duration of chemical etching.

FIG. 10A-C shows microscopy images of a portion of the cathode cup with a second pattern exposed to a third duration of chemical etching. In one example, the third duration may be 15 minutes and the chemical etchant used for etching the surface may be ferric chloride. The second pattern may include pyramid like protrusions 1022 formed on a surface (such as patterned surface 610 in FIG. 6) of the cathode cup (such as cathode cup 352 in FIG. 6). Each pyramid like protrusion 1022 may include angled walls 1044 leading to a tip 1046. The protrusions 1022 may be symmetrically distributed on a surface 1010 of the cathode cup.

Figure 12:
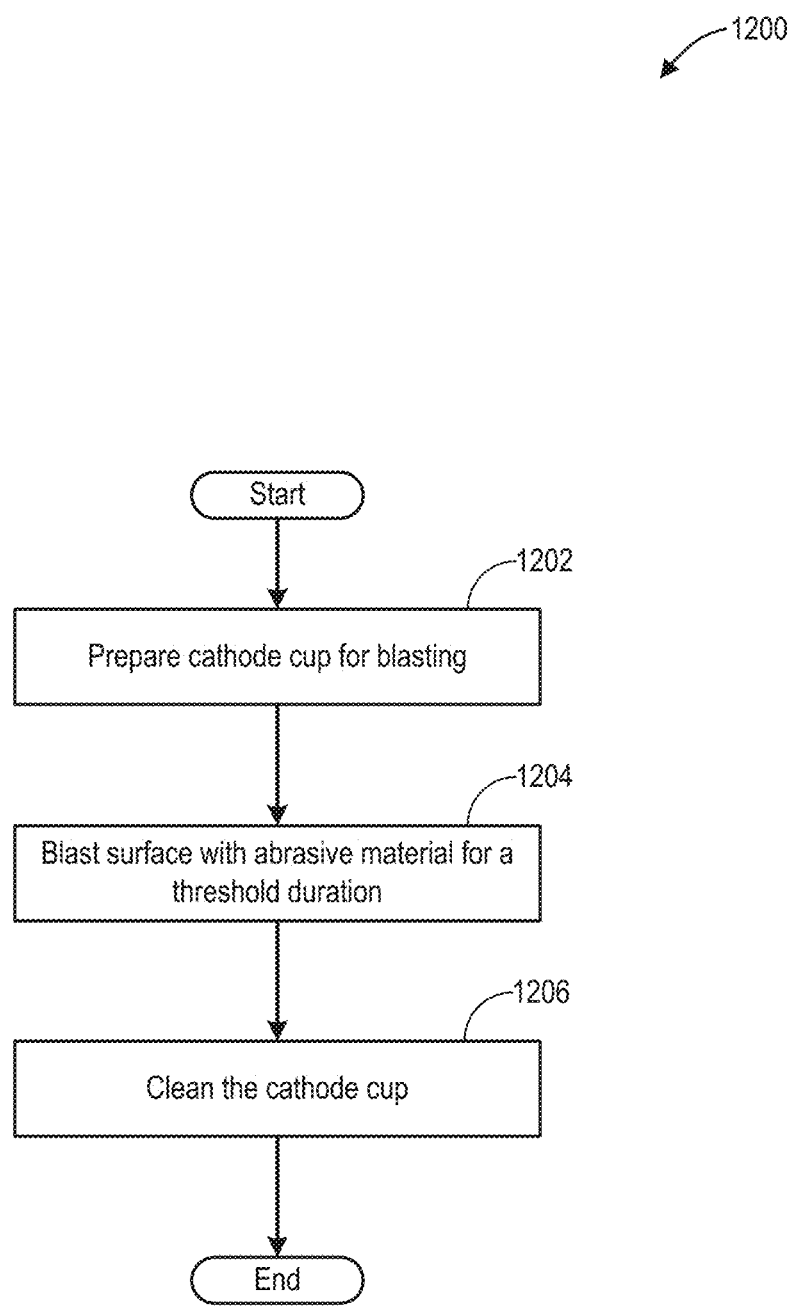
FIG. 12 shows a flow chart of an example method for texturing a cathode cup via mechanical blasting.

The first image 1020 as shown in FIG. 10A is captured at a first magnification via a scanning electron microsphere (SEM). The second image 1040 as shown in FIG. 10B is captured at a second magnification via SEM and the third image 1060 as shown in FIG. 10C is captured at a third magnification via SEM. The third magnification may be higher than each of the first and the second magnification and the second magnification may be higher than the first magnification. As seen from the images, upon exposure to the chemical etchant for the third duration, textures 1042 form on the protrusions 1022 and the surface 1010. The material at the grain boundaries of the material of the surface are etched away (eroded) to form a rougher surface. A distance between features (such as adjacent grains) may be in the range 100 nm and 200 µm, and the grain boundaries may have a depth in the range of 10 µm and 200 µm. The texture provides microscopic edges and cavities where the sublimated material from the emitter may lodge and be retained for a longer duration. Texturing on a surface of the cathode cup may also be attained via a mechanical process such as blasting. FIG. 12 shows an example method 1200 for texturing a cathode cup (such as cathode cup 352 in FIG. 6) via mechanical blasting. One or more surfaces of a cathode cup exposed to deposits from an emitter may be textured at a microscopic level. The surfaces of the cathode cup that are textured may include the bottom surface (such as bottom surface 356 in FIG. 6), the sidewalls (such as sidewalls 358 in FIG. 6), and the patterned surface (such as surface 610 in FIG. 6) including the protrusions of the cathode cup.

At 1202, the surfaces of cathode cup may be prepared for blasting. Preparing the surfaces for blasting may include cleaning the surfaces with water and/or a cleaning solution and the drying the surface. Preparing the cathode surfaces may further include providing a mask to shield regions not to be textured.

At 1204, the surface to be textured may be blasted with an abrasive material for a threshold duration. A stream of the abrasive material may be forcibly propelled from a dispenser at high pressure and upon encountering the surface to be textured, material may be removed from the surface, thereby increasing its surface roughness. The abrasive material may corrode the grains on the surface of the cathode cup, accentuating the grain boundaries causing unevenness. Example abrasive materials used for blasting may include metal pellets, sand, glass beads, and plastic beads. In one example, the entire area of the surface may be blasted at once by directing the abrasive material on the entire surface to be textured. In another example, the dispenser of the abrasive material may scan the entire surface area and propel the abrasive material on a smaller area at a time. A path of travel of the dispenser may be programmed such that the entire surface area is covered. A level of microscopic texturing (sculpting) attained may be based on the abrasive material used and the duration of blasting, the level of texturing increasing with the duration of blasting. An amount of sculpting desired on the surface may include a threshold distance between adjacent grain boundaries and a threshold depth of grain boundaries. As an example, the threshold distance may be in a range of 100 nm and 10 mm, and the threshold depth being in a range of 10 μm and 10 mm. In one example, the threshold distance may be in a range of 100 nm and 1000 μm and the threshold depth being in a range of 10 μm and 1000 μm. In another example, the threshold distance may be in a range of 100 nm and 200 μm, and the threshold depth being in a range of 10 μm and 200 μm.

Upon completion of attainment of the amount of sculpting desired, blasting of the surface with the abrasive material may be discontinued, and, at 1206, the surface of the cathode cup that is being textured may be cleaned and all remaining abrasive material may be removed from the surface. The surface may be wiped with water or a cleaning solution.

In this way, a surface of a cathode cup may be sculpted with microstructures chemically and/or mechanically to form a plurality of features with a higher than threshold depth of each feature, the surface of the cathode cup facing an emitter coupled to the cathode cup. While the above embodiments illustrate chemical and mechanical etching processes to sculpt the surfaces of the cathode cup, additionally or alternatively, heat treatment may be employed, for example, in order to further increase coarseness of the microstructures/features.

In one example, a method, comprises: chemically and/or mechanically texturing a surface of a cathode cup to form a plurality of features with a higher than threshold depth of each feature and greater than a threshold distance between two adjacent features, the surface of the cathode cup facing an emitter coupled to the cathode cup. In the preceding example, additionally or optionally, the chemically texturing includes chemically etching the surface with a chemical etchant. In any or all of the preceding examples, additionally or optionally, chemically etching includes dispensing an amount of a chemical etchant onto the surface and exposing the surface to the chemical etchant for a higher than threshold duration. In any or all of the preceding examples, additionally or optionally, dispensing the chemical etchant includes adding the chemical etchant to the surface via one or more of a pipette, a syringe, and a dropper. In any or all of the preceding examples, additionally or optionally, dispensing the chemical etchant further includes, dabbing the chemical etchant in a swab and lathering the chemical etchant on the surface with the swab. In any or all of the preceding examples, additionally or optionally, one or more of a concentration of the chemical etchant dispensed on the surface and a contact duration of the chemical etchant with the surface is directly proportional to a level of texturing to be attained on the surface, the one or more of concentration of chemical etchant and the contact duration increasing with the level of texturing. In any or all of the preceding examples, additionally or optionally, the level of texturing includes a distance between two adjacent features and a depth of each feature, the level of texturing increasing with each of a decrease in the distance between two adjacent features and an increase in the depth of each feature. In any or all of the preceding examples, additionally or optionally, each feature is any of a grain, a grain boundary, and a phase of a material constituting the surface. In any or all of the preceding examples, additionally or optionally, the depth of each feature is in a range of 10 μm and 10 mm and wherein the distance between two adjacent features is in a range of 100 nm and 10 mm. In any or all of the preceding examples, additionally or optionally, mechanical texturing includes blasting the surface with a medium for another threshold duration. In any or all of the preceding examples, additionally or optionally, blasting includes propelling the medium on the surface from a dispenser at an elevated pressure for the another threshold duration. In any or all of the preceding examples, additionally or optionally, each of the threshold duration of exposure of the surface to the chemical etchant and the another threshold duration of blasting is based on the level of texturing to be attained on the surface. In any or all of the preceding examples, additionally or optionally, the threshold depth of each feature is in a range of 1 μm and 10 μm.

Another manufacturing method comprises: sculpting a surface of a cathode cup of an x-ray tube with microstructures including: coating the surface with a chemical etchant; and exposing the surface to the chemical etchant for a threshold duration to etch grain boundaries of a material of the surface, the threshold duration based on an amount of sculpting desired. In the preceding example, the method further comprising, additionally or optionally, blasting the surface with an abrasive material to attain the microstructures with a surface roughness proportional to a particle size of the abrasive material. In any or all of the preceding examples, additionally or optionally, the abrasive material includes one or more of metal pellets, sand, glass beads, ceramic beads, and plastic beads, and wherein the chemical etchant includes any of an acidic compound and a basic compound, the acidic compound including any of hydrofluoric acid (HF), sulfuric acid ($H_2SO_4$), nitric acid ($HNO_3$), hydrochloric acid (HCl), ferric chloride, or any combination thereof, and the basic compound including any of sodium hydroxide (NaOH), potassium hydroxide (KOH), ammonium hydroxide ($NH_4OH$) or any combination thereof. In any or all of the preceding examples, additionally or optionally, the amount of sculpting desired is a threshold distance between adjacent grain boundaries and a threshold depth of grain boundaries, the threshold distance being in a range of 100 nm and 10 mm and the threshold depth being in a range of 10 μm and 10 mm.

In yet another example, a system, comprises: a surface of a cathode cup of an x-ray tube facing an emitter formed of a material; the surface including a plurality of etched features with grains boundaries of the material having a higher than threshold depth of 1 μm to entrap sublimated material from the emitter. In the preceding example, additionally or optionally, the plurality of etched features include a distance between two adjacent features being in the range of range of 100 nm and 10 mm. In any or all of the preceding examples, additionally or optionally, the material forming the surface of the cathode cup is one of nickel, molybdenum, Fe-41.5Ni (Ni42), Fe-29Ni-17Co (Kovar), or niobium, and wherein the emitter is made of tungsten.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   chemically and/or mechanically texturing a surface of a cathode cup to form a plurality of features with a depth of each feature falling within a first range of 1 μm to 1 mm and a distance between two adjacent features falling within a second range of 100 nm to 1 mm, the textured surface of the cathode cup facing configured to face an emitter configured to couple to the cathode cup.

2. The method of claim 1, wherein the chemically and/or mechanically texturing includes chemically etching the surface with a chemical etchant.

3. The method of claim 2, wherein chemically etching includes dispensing an amount of a chemical etchant onto the surface and exposing the surface to the chemical etchant for a duration.

4. The method of claim 3, wherein dispensing the chemical etchant includes adding the chemical etchant to the surface via one or more of a pipette, a syringe, and a dropper.

5. The method of claim 3, wherein dispensing the chemical etchant includes dabbing the chemical etchant in a swab and lathering the chemical etchant on the surface with the swab.

6. The method of claim 3, wherein one or more of a concentration of the chemical etchant dispensed on the surface and a contact duration of the chemical etchant with the surface are selected based on a level of texturing to be attained on the surface, the one or more of concentration of chemical etchant and the contact duration increasing with the level of texturing.

7. The method of claim 3, wherein chemically and/or mechanically texturing includes blasting the surface with an abrasive material for another duration.

8. The method of claim 7, wherein blasting includes propelling the abrasive material on the surface from a dispenser for the other duration.

9. The method of claim 7, wherein each of the duration of exposure of the surface to the chemical etchant and the other duration of blasting is based on the level of texturing to be attained on the surface.

10. The method of claim 1, wherein each feature is any one of a grain and a grain boundary of a material constituting the surface.

11. The method of claim 1, wherein the depth of each feature falls within a third range of 1 μm to 10 μm.

12. A manufacturing method, comprising:
    forming a patterned surface in a cathode cup of an x-ray tube; and
    texturing the patterned surface to form microstructures on the patterned surface, the texturing including:
    coating the patterned surface with a chemical etchant; and
    exposing the patterned surface to the chemical etchant for a duration to etch grain boundaries of a material of the patterned surface, the duration based on an amount of texturing desired.

13. The method of claim 12, wherein the cathode cup includes one or more additional surfaces, wherein texturing the patterned surface includes also texturing the one or more additional surfaces to form microstructures on the one or more additional surfaces, and further comprising, blasting the patterned surface and one or more additional surfaces with an abrasive material to form the microstructures, where the textured patterned surface has a surface roughness proportional to a particle size of the abrasive material.

14. The method of claim 13, wherein the patterned surface is a bottom surface of the cathode cup and the one or more additional surfaces are side surfaces of the cathode cup, wherein texturing the patterned surface and the one or more additional surfaces comprises texturing the patterned surface to a first level of texturing and texturing the one or more additional surfaces to a second, different level of texturing, wherein the abrasive material includes one or more of: metal pellets, sand, glass beads, ceramic beads, and plastic beads, and wherein the chemical etchant includes one or more of: an acidic compound and a basic compound, the acidic compound including hydrofluoric acid (HF), sulfuric acid ($H_2SO_4$), nitric acid ($HNO_3$), hydrochloric acid (HCl), ferric chloride, or any combination thereof, and the basic compound including sodium hydroxide (NaOH), potassium hydroxide (KOH), ammonium hydroxide ($NH_4OH$), or any combination thereof.

15. The method of claim 12, wherein the etching of the grain boundaries includes etching the grain boundaries so that a distance between adjacent grain boundaries falls within a range of 100 nm to 10 mm and a depth of the grain boundaries falls within a range of 10 μm to 10 mm, and wherein forming the patterned surface comprises forming the patterned surface with an end milling process, electrical discharge milling (EDM), plunge EDM, or knurling.

16. A cathode for an x-ray tube, comprising:
    an emitter; and
    a cathode cup positioned to hold the emitter, the cathode cup including a surface facing the emitter, the surface of the cathode cup formed of a material having grain boundaries etched to a depth in a range of 1 μm to 1 mm to entrap sublimated material from the emitter.

17. The system of claim 16, wherein a distance between any two adjacent grain boundaries is in a range of 100 nm to 10 mm.

18. The system of claim 16, wherein the material forming the surface of the cathode cup is any one of nickel, molybdenum, Fe-41.5Ni (Ni42), Fe-29Ni-17Co (Kovar), or niobium, wherein the emitter is made of tungsten, and wherein the x-ray tube comprises an anode and the emitter is configured to generate electrons that accelerate towards and collide with the anode.

* * * * *